US005759820A

United States Patent [19]

Hornes et al.

[11] Patent Number: 5,759,820
[45] Date of Patent: *Jun. 2, 1998

[54] PROCESS FOR PRODUCING CDNA

[75] Inventors: Erik Hornes; Lars Korsnes, both of Oslo, Norway

[73] Assignee: Dynal AS, Oslo, Norway

[*] Notice: The term of this patent shall not extend beyond the expiration date of Pat. No. 5,572,439.

[21] Appl. No.: 280,133

[22] Filed: Jul. 25, 1994

Related U.S. Application Data

[63] Continuation of Ser. No. 688,936, filed as PCT/EP89/01418, Nov. 21, 1989, published as WO90/06044, Jun. 14, 1990.

[30] Foreign Application Priority Data

Nov. 21, 1988 [GB] United Kingdom ............ 8827158
Nov. 21, 1988 [GB] United Kingdom ............ 8827159

[51] Int. Cl.$^6$ ............... C12P 19/34; C12Q 1/68; C12Q 1/70; B01J 19/08

[52] U.S. Cl. ............... 435/91.1; 435/6; 435/5; 435/91.2; 435/173.9; 422/186.01; 422/186.03; 204/156; 204/554; 436/125; 436/126; 536/24.3; 536/24.32; 536/24.33

[58] Field of Search ............... 435/6, 91.2, 5, 435/91.1, 173.9; 436/125, 126; 204/660, 156, 554; 422/186.01, 186.03; 536/24.3–24.33

[56] References Cited

U.S. PATENT DOCUMENTS

| | | | |
|---|---|---|---|
| 4,683,202 | 7/1987 | Mullis | 435/91 |
| 4,695,392 | 9/1987 | Whitehead et al. | 252/62.54 |

FOREIGN PATENT DOCUMENTS

| | | | |
|---|---|---|---|
| 0184056 | 6/1986 | European Pat. Off. | C07H 21/00 |
| 0223618A2 | 5/1987 | European Pat. Off. | C12Q 1/68 |
| 0297379 | 6/1987 | European Pat. Off. | C12Q 1/68 |
| 0265244A1 | 4/1988 | European Pat. Off. | G01N 33/538 |
| 0288737A1 | 11/1988 | European Pat. Off. | C12Q 1/68 |
| 8303920 | 11/1983 | WIPO | H01F 1/09 |
| WO85/04674 | 10/1985 | WIPO | C12P 19/34 |
| WO88/07585 | 10/1988 | WIPO | C12Q 1/68 |

OTHER PUBLICATIONS

Jongstra et al. The isolation and sequence of a novel gene from a human functional T–cell line, J. Exp. Med. (Mar. 1987) 165:601–614.
Scott et al. Activation of mouse genes in transformed cells. (Sep. 1983) 34:557–567.
Venetiauer, P. et al. Proc. Natl. Acad Sci. USA (Oct. 1974) 71:3892–3895.
Kuribayashi et al., "A rapid and efficient purification of poly(A)–mRNA by oligo(dT)$_{30}$–Latex", *Nucleic Acids Research*, Symposium Series No. 18, pp. 61–64 (1988).
Atkinson et al., "A convenient procedure for the synthesis of oligodeoxyribonucleotide affinity columns for the isolation of mRNA", *Nucleic Acids Research*, 16:6232 (1988).
Okayama et al., "A cDNA Cloning Vector That Permits Expression of cDNA Inserts in Mammalian Cells", *Molecular and Cellular Biology*, 3:280–289 (1983).
Okayama et al., "High–Efficiency Cloning of Full–Length cDNA", *Molecular and Cellular Biology*, 2:161–170 (1982).
Nucleic Acids Research, vol. 16, No. 7 pp. 3025–3028, Apr. 11, 1988, Stefan Stahl et al.
Nucleic Acids Research, vol. 15, No. 13, Jul. 10, 1987, pp. 5373–5389, Gingeras et al.
Nature, vol. 308, pp. 149–153, Mar. 8, 1984, Hedrick et al.
Cell vol. 21, pp. 709–715, Oct. 1980, Zimmerman et al.

*Primary Examiner*—W. Gary Jones
*Assistant Examiner*—Dianne Rees
*Attorney, Agent, or Firm*—Foley and Lardner

[57] ABSTRACT

The process includes the steps of: a) contacting a liquid containing mRNA with an insoluble support having DNA probes attached thereto via the 5'-terminus thereof whereby the MRNA is hybridized to said probes and hence to said support; b) removing said liquid; and c) adding enzymes and nucleotides in solution whereby the probe functions as a primer to produce single stranded cDNA on the mRNA probe. The probe DNA may be oligo-dT or a specific DNA sequence, such as one that is complementary to a conserved region in a class of mRNA molecules. The insoluble support comprises magnetic particles which are monodisperse polymer particles comprising superparamagnetic iron oxide, a coating to reduce non-specific binding and a substituent for attaching an oligonucleotide.

12 Claims, No Drawings

PROCESS FOR PRODUCING CDNA

This application is a continuation of application Ser. No. 07/688,936, filed May 14, 1991 (which is a 371 application of PCT/EP89/01418 filed on Nov. 21, 1989).

This invention relates to a rapid process for producing cDNA and a kit for carrying out such a process.

The conventional method of producing cDNA from RNA is that described by Maniatis at el (Molecular Cloning: a laboratory manual (1982) Cold Spring Harbor Laboratory). Briefly, this process can be divided into four stages.

1. Cytoplasmic RNA is isolated from a cell culture in the presence of ribonuclease inhibitors.
2. Cytoplasmic RNA is passed through an oligo- dT column and mRNA is bound to the oligo-dT via its polyadenylate (poly A) tail. The column is washed and the mRNA is then eluted from the column. This mRNA may then be size fractionated, usually using column chromatography or agarose gel electrophoresis.
3. The gel fraction containing a specific target mRNA may be identified by in vitro translation in a rabbit reticulocyte lysate system.
4. An oligo-dT primer is then hybridised to the mRNA which is then treated with reverse transcriptase to produce single stranded cDNA (ssDNA), the mRNA is removed, and double stranded cDNA (ds cDNA) is formed using a polymerase.

The ds cDNA can then have appropriate linkers provided at each end and be inserted into a plasmid. This is normally effected using a large excess of the linker reagent.

A great deal of time and care is required when performing this conventional process. mRNA is rapidly lost by hydrolysis and degradation even in the presence of ribonuclease inhibitors. Further losses of the sought after mRNA occur at the steps of elution from the column and size fractionation. Furthermore, excess linker reagent has to be carefully separated before introduction of the dscDNA into the plasmid.

There is thus a need to provide a simple and rapid process for the production of cDNA. An object of this invention is to meet that need.

The present invention is based on the concept of isolating mRNA on an insoluble support and then forming cDNA without the intervening steps of elution from a column, size fractionation and repriming.

Accordingly, the invention provides a process for the production of cDNA which includes the steps of:

a) contacting a liquid containing mRNA with an insoluble support having DNA probes attached thereto via the 5'-terminus thereof whereby the mRNA is hybridised to said probes and hence to said support;

b) removing said liquid; and c) adding enzymes and nucleotides in solution whereby the probe functions as a primer to produce single stranded cDNA on the mRNA templates.

Where the mRNA is contained in said liquid together with contaminants, the mRNA bound to the insoluble support may be washed between steps (b) and (c) to ensure removal of such contaminants.

The ssDNA can, if required, be converted into dsDNA by conventional methods, for example:

(1) removing the mRNA template by denaturation and adding enzymes and nucleotides in solution to produce double stranded DNA;
(2) adding RNase H to remove the mRNA and DNA polymerase to form the required second DNA strand;
(3) removing the mRNA template, adding a number of short DNA primers to hybridise to homologous sequences of the sscDNA and then adding a DNA polymerase and a ligase to form the required second DNA strand (Multiprimer method).

Likewise, the insoluble support may be washed between steps (c) and (1) and between steps (1), (2) and (3).

The probes can be DNA moieties which will hybridise with mRNA and are preferably oligo-dT, which will hybridise with the poly A 'tails' universally present on native mRNA. However, probes may comprise specific DNA sequences which hybridise with specific sequences in target RNA molecules which may for example be conserved sequences in families of related RNA molecules. Each probe may consist of a directly attached single stranded DNA which may be oligo-dT or a specific DNA sequence or it may be attached to the insoluble support via a double stranded piece of DNA.

A particularly useful form of probe for use where one wishes to isolate mRNA for subsequent cDNA synthesis is a DNA sequence in which the 3' end overlaps and is hybridised to a region near the 5' end, leaving the remainder of the 5' -terminal region as a sticky end to hybridise with the target nucleic acid. If a functional group such as an amino group is present in a position distal from the sticky end, the loop may be covalently attached to the insoluble support e.g. via carboxyl groups. Alternatively, a biotin group may be attached to the loop and thus bind the probe to an avidin or streptavidin coated support. DNA having a terminal region corresponding to the sticky end will thus have the possibility of being ligated to the adjacent part of the loop if it is required to secure the DNA covalently. RE sites can be provided in the overlap region of the probe for subsequent detachment of the DNA.

Oligo-dT probes, that is relatively short chains of deoxythymidine units, e.g. from 20 to 200 bases, may be readily and cheaply prepared by enzymic polymerisation of deoxythymidine units, e.g. from 20 to 200 bases. Also, probe and primer oligonucleotides may be prepared by using any of the commercially available DNA synthesis devices, e.g. those available from Applied Biosystems, Inc. (850-T Lincoln Center Drive, Foster City, Calif. 94404).

To avoid random hybridisation of unwanted nucleic acid and to complete the removal of the remaining components of the hybridisation solution, the insoluble support is preferably washed at least once after separation. To remove nucleic acid bound by random partial homology, the washing may be carried out under stringent conditions, either by increasing the temperature or by using a lower salt concentration than that used in hybridisation, e.g. 0.5M sodium chloride or an equivalent solution.

Stringency is normally calculated according to the probe length and G:C content. If the homology between the probe oligonucleotide and the target nucleic acid is inexact, washing should be carried out under less stringent conditions. In general, washing should be carried out at a temperature 12° C. below the melting temperature of the duplex ($T_m$). The approximate $T_m$ may be conveniently calculated according to the following relationships (taken from Maniatis, T. et al (1982) Molecular-Cloning; a laboratory manual pages 388–389).

(a) $T_m = 69.3 + 0.41 \cdot (G+C)\% - 650/L$

L equals the average length of the probe in nucleotides.

(b) The $T_m$ duplex DNA decreases by 1° C. with every increase of 1% in the number of mismatched base pairs.

(c) $(T_m)u_2 - (T_m)u_1 = 18.5 \log_{10} \frac{u_2}{u_1}$ where $u_1$ and $u_2$ are the ionic strengths of two solutions.

For small oligonucleotides, the melt temperature may be approximated in degrees centigrade as follows:

$T_m = 2 \times (\text{number of A+T residues}) + 4 \times (\text{number of G+C residues})$ The hybridisation reaction is preferably effected in a 1M sodium chloride solution or an equivalent solution known in the art. (See Nucleic Acid Hybridisation, B. D. Hames and S. J. Higgins, IRL Press, 1985).

In conventional methods enzymic operations are often carried out in the same unchanged buffer which is thus not optimised for each reaction. However, the method according to the invention allows one to change buffers and the like and thereby optimise the production of cDNA. Further, in conventional ss cDNA synthesis, the ratio of nucleotide reagents to mRNA is usually kept approximately stoichiometric in order to avoid contaminating succeeding stages with excess reagent. The ease and speed of washing, which comes from immobilisation of target nucleic acid according to the invention, permits excess reagents to be used, with a consequent increase of efficiency.

The insoluble support may take a variety of forms, for example microtitre wells, filters made from materials such as cellulose or nylon, or particles including, for example, sephadex or sepharose beads or polystyrene latex particles. It is a preferred feature of the invention to use magnetic particles which may be magnetically aggregated onto a surface and then be readily re-dispersed for a subsequent treatment step, e.g. by physical agitation.

Advantageously the particles are monodisperse and/or superparamagnetic. Both these properties greatly assist the kinetics of reactions in which the particles are involved. It is a surprising feature of the invention that the probes carried by the particles react in the reactions virtually as rapidly as if free in solution. For example, total purification of mRNA can be effected in less than 15 minutes which contrasts sharply with the 2 hours required for purification of mRNA onto a poly-dT affinity column. By using monodisperse particles, that is particles of substantially the same size, the reaction rate and other parameters are particularly uniform. By using superparamagnetic particles (that is particles containing sub-particles of ferromagnetic material which are smaller than the domain size required to maintain permanent magnetism), one can avoid magnetic aggregation or clumping of the particles during reaction, thus again ensuring uniform and rapid reaction kinetics. Thus, the particles can readily be aggregated at a uniform speed onto a surface by application of a magnetic field but can readily be re-dispersed for a subsequent treatment step, e.g. by physical agitation. This uniformity of behaviour and rapidity of reaction lends itself particularly to automation, which is an essential requirement of many of the nucleic acid manipulations required in commercial production and/or repetitive processes. It is most important that the reactions and separations can be carried out completely reliably by an appropriate machine with minimal human intervention.

The preferred magnetic particles for use in this invention are monodisperse superparamagnetic beads produced according to EP 83901406.5 (Sintef), the disclosure of which is incorporated herein by reference. In these beads, the iron is very uniformly distributed and provides a very uniform response to a magnetic field which is important in designing a reproducible procedure, particularly for automation, since all the beads move at the same speed. Furthermore, since a reproducible amount of iron can be incorporated in each particle, this can be adjusted to a relatively low level which permits the specific gravity of the particles to be in the range specified below. In the case of prior, less regular products, small particles either had too little iron to counteract Brownian forces when a magnet was applied or the specific gravity of the material led to undesirable sedimentation of the larger particles. Some automated systems use magnetic fields to restrain the particles within a reaction zone while solutions are passed through; uniform magnetic and rheological properties are essential in magnetic particles for use in such a system.

The term "monodisperse" used herein is intended to encompass size dispersions having a diameter standard deviation of less than 5%.

We prefer to use beads having a specific gravity in the range 1.1 to 1.8 most particularly 1.2 to 1.5. In the monodisperse beads used in accordance with the invention, the specific gravity is, again, particularly uniform, leading to uniform and predictable kinetic characteristics.

Advantageously, the monodisperse particles are spherical beads of diameter at least 1 and preferably at least 2 microns, being preferably not more than 10 and more preferably not more than 6 microns in diameter e.g. about 3 microns. Smaller particles sediment more slowly and in some cases the sedimentation time may be long compared to the reaction time, thus avoiding the need for physical agitation. However, particles of mean diameter 0.1 to 1.5 microns including fine particles of much smaller diameter, as used in the prior art, behave unreliably in response to magnetisation.

The attachment of the probes to the particles may be by direct chemical bonding as well as affinity binding, by streptavidin/biotin complexes and the like.

For attachment of the probes, the magnetic particles may carry functional groups such as hydroxyl, carboxyl, aldehyde or amino groups. These may in general be provided by treating uncoated monodisperse, superparamagnetic beads, to provide a surface coating of a polymer carrying one of such functional groups, e.g. polyurethane together with a polyglycol to provide hydroxyl groups, or a cellulose derivative to provide hydroxyl groups, a polymer or copolymer of acrylic acid or methacrylic acid to provide carboxyl groups or an aminoalkylated polymer to provide amino groups. U.S. Pat. No. 4654267 describes the introduction of many such surface coatings.

Preferred coated particles for use in the present invention may be prepared by modification of the beads according to the U.S. Pat. Nos. 4,336,173, 4,459,378 and 4,654,267, the disclosure of which is incorporated herein by reference. Thus, for example, macroreticular porous polymer particles, prepared from styrene-divinylbenzene and with a diameter of 3.15 um were treated with $HNO_3$ to introduce $-NO_2$ groups at the surface of the pores. Then the particles were dispersed in an aqueous solution of $Fe^{2+}$. The $Fe^{2+}$ is oxidised by the $-NO_2$ groups which leads to precipitation of insoluble iron oxy-hydroxy compounds inside the pores. After heating the iron exists as finely divided grains of magnetic iron oxides throughout the volume of the porous particles. The $No_2$ groups are reduced by the reaction with $Fe^{++}$ to $NH_2$ groups.

To fill up the pores and to introduce the desired functional groups at the surfaces, different monomers are caused to polymerize in the pores and at the surface. In the case of a preferred type of particle, the surface carries –OH groups connected to the polymeric backbone through $-(CH_2CH_2O)_{8-10}$ linkages. Other preferred beads carry —COOH groups obtained through polymerization of methacrylic acid.

Thus, for example, the NH$_2$ groups initially present in the beads may be reacted with a diepoxide as described in U.S. Pat. No. 4654267 followed by reaction with methacrylic acid to provide a terminal vinyl grouping. Solution copolymerisation with methacrylic acid yields a polymeric coating carrying terminal carboxyl groups as in R452 beads referred to below.

Similarly, amino groups can be introduced by reacting a diamine with the above product of the reaction with a diepoxide as in the R240, R442 and R469 beads, while reaction with a hydroxylamine such as aminoglycerol introduces hydroxy groups as in the M450 and L255 beads. DYNABEADS M450(diameter 4.5 microns) which may be obtained from Dynal, Oslo, Norway have been coated with a monomeric epoxide, resulting in a mixture of epoxy and hydroxy groups. Contact with water however, converts the epoxy groups to hydroxy groups.

DYNABEADS M 280 (diameter 2.8 microns) are polystyrene beads having hydroxyl groups which have been converted into tosyloxy groups by reaction with p-toluene sulphonyl chloride.

Using functionalised coatings of the above types, we have found the non-specific binding of DNA and/or RNA to be very low, particularly in the case of the carboxylated beads.

As indicated above, the probe and RE linker are preferably attached to the magnetic particles via carboxyl groups, the DNA being firstly provided with a 5'-terminal amino group which can be made to form an amide bond with the carboxyl using a carbodiimide coupling agent. 5'-attachment of DNA can also be effected using hydroxylated magnetic particles activated with CNBr to react with 5'-amino DNA.

The 3'-attachment of the oligonucleotide DNA can also be effected by chemical synthesis. Here again, the very uniform nature of the monodisperse particles provides uniform reaction rates particularly suited to synthesis in an automated synthesiser such as the Gene Assembler (Pharmacia AS). The magnetic particle needs to be provided initially with a hydroxyl or protected hydroxyl group. DYNABEADS M-280 of Dynal A/S are well suited to this purpose. If necessary, however, other surface functions such as carboxyl could be used to attach a linker carrying a hydroxyl group or alternatively a 3'-attached nucleotide.

5'-Attachment may be effected by coupling of 5'-aminooligonucleotides to tosyl-activated magnetic particles. The latter may be produced by tosylation of hydroxylated magnetic particles such as DYNABEADS M-28 of Dynal A/S. Displacement of the tosyloxy group leaves the 5'-amino group directly attached to the magnetic beads.

Since biotin labelled nucleotides are commercially available, the 3'-end of DNA fragments can be labelled using DNA polymerase and these may be conveniently bound to avidin or streptavidin attached to the magnetic particles e.g. via a hydroxy group. The biotin label may be attached to the nucleotide by a spacer arm, such as one or more e-aminocaproic acid moieties, to minimize steric hindrance.

In general, the functionalisation of the beads and subsequent attachment of probes is advantageously such that each magnetic particle carries $10^3$–$10^6$ probes. (1–300 pmols per mg). The uniform size of the magnetic particles is of advantage in ensuring uniform probe density when the probes are reacted with the particles. Uniform probe density is important in ensuring that all the probes behave in substantially the same way in the various procedures in which they are used.

It is a remarkable feature of the magnetic particles that enzyme activity appears to take place very close to the particle surface e.g. within 7 bases. Thus, if an RE site is present in a linker sequence as discussed hereinafter and if the probe is subsequently used as a primer, it is found that sscDNA and hence ds cDNA can be synthesised by the DNA polymerase past the RE site towards the bead surface and can thus itself readily be cleaved by the appropriate endonuclease. In the case of the carboxylated beads, it is found that the micro-surface of the beads is extremely irregular, presenting an unusually large surface area which may reduce steric hinderance to hybridisation and enzyme activity close to the surface. On the other hand the non-specific binding to such carboxylated beads is not increased. However, for some uses it may be desirable to have only a single probe per bead. The specific surface area of the magnetic particles is generally in the range 2 to 50 m$^2$ per gram. In general, the number of probes per m$^2$ is in the range 20 to 50×10$^5$. The extreme uniformity of the magnetic particles greatly facilitates control of the probe density within close limits.

cDNA synthesis according to the invention may be of use in many different contexts, for example total conversion of cellular mRNA to cDNA to avoid problems arising from the instability of mRNA, site directed mutagenesis are as described in our application of even date herewith corresponding to United Kingdom Patent Application No. 8817267.1 detection and quantification of target nucleic acids as described in our copending application of even date herewith corresponding to United Kingdom Patent Application No. 8817260.6 and production of DNA for cloning.

The invention can be used with particular advantage in subtraction cDNA library construction. Such libraries are particularly useful in the study of cell differentiation or modification.

One prior art method of studying cell differentiation involves two dimensional gel chromatography of protein cell extracts. The proteins become separated by virtue of the size and the charge which they carry when a charge is applied to the gel. The pH and salt concentrations differ for the first and second directions. Once a protein cell extract has undergone two-dimensional gel chromatography it is developed, i.e. stained in some way. The appearance and disappearance of proteins during cellular differentiation can be monitored by the presence or absence of spots on the developed gel.

The above method of studying differentation is very time consuming. Glycosylated proteins appear as smears on the gels, since the level of glycosylation varies. The amounts of proteins isolated are very small and do not lend themselves to further study.

There is a great need for a method of studying cell differentiation which is not only rapid but also provides a route to obtaining sufficient quantities of the proteins involved in differentation for further study. In addition to natural cell differentiation, it is also of great interest to study the products of cell transformation, stimulation and/or virus infection.

A further aspect of the present invention is based on the separation of mRNA from a first population of cells, reverse transcribing to form a corresponding first strand cDNA library and using this library to extract the mRNA from the total mRNA of a second cell population to leave behind the mRNA present only in the second cell population.

The present invention provides, in a further aspect, a process for the production of a subtraction cDNA library relative to a population of cells and a modified population of those cells including the steps of:

a) contacting a liquid containing the total mRNA from a first one of said cell populations with an insoluble support carrying 5'-attached oligo-dT probe whereby substantially all said mRNA is hybridised thereto;

b) removing said liquid;
c) using said oligo-dT probe as a primer contacting the insoluble support with a reverse transcriptase whereby corresponding single strands of cDNA are formed and removing the hybridised mRNA to provide a cDNA library attached to said insoluble support;
d) contacting the insoluble support carrying attached first strand cDNA with a liquid containing the total mRNA of the second one of said two cell populations to hybridise mRNA present in both cell populations; and
e) removing the insoluble support and attached mRNA to leave in solution those mRNA molecules present only in said second cell population.

The modification of an initial cell population can cause both the introduction or activation of genes, thereby producing added mRNA species, or removal or switching off of genes, thereby preventing production of certain mRNA species. Consequently, it is of interest to isolate mRNA (and hence produce cDNA libraries) corresponding to both the added and the eliminated mRNA.

The mRNA newly formed by the modified cells can be isolated by choosing the unmodified cell population as the first cell population in the process of the invention, the modified cells being the second cell population. Conversely, the mRNA eliminated by cell modification may be isolated by choosing the modified cells as the first cell population and the unmodified cells as the second cell population.

The residual mRNA isolated in the above way may then be used to make a subtraction cDNA library by any desirable route. Such routes include binding the mRNA to a insoluble support having oligo-dT probes attached thereto and the reverse transcribing to give single stranded cDNA, as described above.

The single stranded cDNA can be turned into double stranded cDNA, provided with a suitable 'sticky' end at the 3' terminus, e.g. a Hind III linker, inserted into a vector by conventional techniques and cloned. The cDNA can thus be transcribed and translated to give proteins either introduced or eliminated by cell modification.

This further method of the invention is advantageously performed with magnetic particles as the insoluble support and will now be described in greater detail with reference to such particles:

A magnetic probe is first prepared having an oligo(dT) sequence. The probe may be of similar construction to the magnetic probes utilized in the solid phase cDNA synthesis described above except that the restriction enzyme site(s) may be optionally omitted. Thus, the magnetic probe comprises an oligonucleotide probe which contains an oligo(dT) sequence coupled through its 5' terminus to a magnetic particle. The magnetic probe is contacted under hybridizing conditions with a suspension or solution of either total RNA, or preferably total mRNA, from the first cell population, i.e. the population in which the gene(s) of interest are repressed. Methods of preparing extracts of total RNA or mRNA are indicated, supra. Typically, about 5 mg of magnetic probe per 50 µg total RNA (or 5 µg purified total mRNA) from the first cell population may be utilized. Hybridization may be conducted at room temperature for ten minutes in a high salt medium, for example 100 µl 6×SSPE which may contain 0.1% SDS (sodium dodecyl sulphate). The magnetic probe is then separated from the hybridization mixture of magnetic separation, carrying along with it the first cell population mRNA, which is coupled to the probe by the hybridization of the probe oligo(dT) sequence to the mRNA poly(A) tail. The probe may then be washed in, e.g., 2×SSC or 6×SSC at 45° C.

The mRNA retrieved with the probe is then reverse transcribed in situ on the magnetic particle as described more particularly above the template mRNA is removed from the DNA/RNA hybrid by, for example, heat treatment at 95° C. for about 5 minutes or alkali treatment for 2 minutes. The magnetic probe, with the ss cDNA hybridized thereto, is magnetically separated. The result is a magnetic ss cDNA library from the first population cells. The library contains ss DNA complementary to mRNA expressed by the first population cells.

Before proceeding further, the oligo(dT) sequence in the probe portion of the magnetic ss cDNA library should be masked to avoid non-specific mRNA binding in the subsequent hybridization step. This may be accomplished by hybridizing to the probe an excess of the appropriate length oligo(A)mer. Thus, for example, wherein the probe oligonucleotide contains a $dT_{25}$ sequence, and the dT sequence resulting from the first strand cDNA synthesis that sequence may be masked by hybridization with an excess of the DNA oligomer $dA_{16}$. In the case where the library is formed using 5 mg of magnetic beads as described above, the oligo(dT) sequence may be masked by incubation with 500 picomoles of the appropriate length oligo(da)mer in 500 µl 6×SSPE. Hybridization of the homopolymer sequences may be achieved by incubation for about ten minutes at room temperature, followed by washing of the magnetic cDNA library in 500 µl 6×SSC at 40° C.

To the first population magnetic ss cDNA library thus formed is added an extract of total RNA or total mRNA from the second population cells, under hybridizing conditions. Hybridization may be carried out, based on 5 mg of magnetic probe as prepared herein, by adding the probe to 20 µg of total RNA (or 20 µg total mRNA) in 200 µl 6×SSPE, pre-warmed at 95° C. for five minutes and quenched on ice. The reactants are gently mixed and allowed to hybridize. Hybridization may be achieved, for example, by incubation for ten minutes at room temperature.

The magnetic probe, now coupled to hybrid duplexes formed of first population ss cDNA and mRNA from the second cell population, is magnetically separated from the reaction mixture. The unhybridized mRNA in the supernatant comprises mRNA from genes repressed in the first population cells, but expressed in the second population cells. The magnetic ss cDNA library may be regenerated by removing the hybridized second cell population mRNA by any convenient method for releasing RNA from RNA/DNA duplexes. According to one such method, the magnetic RNA/DNA duplexes are added to 100 µl of 2×SSC and heat-treated at 95° C. for five minutes to melt away hybridized mRNA. Alternatively, more alkaline conditions may be used together with a lower temperature. The regenerated first population ss cDNA library may be reused in another round of hybridization.

Preferably, the above procedure is carried out utilizing purified total mRNA, rather than purified total RNA. Where total RNA is employed as a source of template RNA, hybridization of the magnetic probe therewith yields somewhat less coupled mRNA per magnetic probe than purified mRNA, owing to interference by non-messenger RNA. The interfering effect of non-messenger RNA can be compensated for, however, by incubating the total RNA with a larger excess of magnetic probe.

Preferably, the differentially expressed mRNA from the second population cells is contacted with additional magnetic first population ss cDNA library, followed by hybridization and magnetic separation, as above. Repetition of this probing step with the first population ss cDNA library insures that all of the mRNA corresponding to the genes expressed in the first population cells will be separated from the differentially expressed second population mRNA. The procedure may be repeated, as desired, to enrich the differential mRNA.

The relative enrichment of the differential mRNA may be conveniently monitored by introducing into the RNA extract from the first population cells an irrelevant control poly(A)-containing RNA. Where, for example, 5 µg purified total mRNA is utilized as the source of template RNA in the generation of the magnetic first population ss cDNA library, 5 nanograms of control mRNA may be added to the purified total mRNA before contact with the magnetic probe. This amount of mRNA corresponds roughly to the amount of RNA which would be expected in the purified total mRNA for a medium- to low-abundance transcript.

A suitably labeled copy of the same control mRNA is also added to the total RNA or mRNA extract from the second population cells. Following hybridization with the magnetic first population ss cDNA library, the amount of labeled control mRNA remaining in the supernatant following magnetic separation is determined.

The label on the control mRNA may comprise any detectable label suitable for labeling nucleic acid. Preferably, the label comprises a radioactive label, such as $^{32}P$ or $^{35}S$. Such radioactive labels may easily be monitored by scintillation counting. Methods of radiolabelling nucleic acids are known to those skilled in the art.

The supernatant containing the second population mRNA not hybridized by the first population magnetic ss cDNA is then utilized as template RNA for cDNA synthesis. A solution or suspension of the unhybridized second population mRNA is contacted under hybridizing conditions with a magnetic probe, as described above, comprising a probe oligonucleotide containing an oligo(dT) sequence covalently coupled through its 5' terminus to a magnetic particle. The probe oligonucleotide further contains a sequence coding for at least one restriction enzyme site. The restriction enzyme site is located upstream of, that is, on the 5' side, of the oligo(dT) sequence. Formation of a complementary cDNA library corresponding to the genes repressed in the first population cells, but expressed in the second population cells, is generated according to the cDNA synthesis method described above. The library is suitably cloned by conventional cDNA cloning techniques.

The existence of differential cDNA clones may be confirmed by any of the various hybridization blotting techniques suitably for detecting specific RNA. Differential cDNA as prepared above, that is, DNA complementary to genes expressed in the second cell population (but not expressed in the first population) is denatured. Single strands thereof are contacted with blotted total RNA from the second population cells. Northernblot or dotblot procedures may be suitably employed for this purpose. The single-stranded differential cDNA will hybridize to the blotted RNA from the second population. Conversely, the differential cDNA will not hybridize to blotted total RNA from the first population cells.

According to a still further feature of the invention there is provided a kit for cDNA synthesis comprising (a) an insoluble support having DNA probes attached thereto, and one or more of the following;

(b) a reverse transcriptase (c) a polymerase and optionally a ligase and/or a nuclease (d) deoxynucleotides (e) appropriate buffers.

The DNA probes will preferably be attached to the support, which will advantageously comprise superparamagnetic particles, via a linker sequence containing an appropriate restriction site.

The following examples are given by way of illustration only:

EXAMPLE 1(a)

Carbodiimide (EDC) mediated attachment of 5'—$NH_2$ probes to carboxyl beads.

(a) The reaction used for attaching probes to carboxyl beads is as follows. Amino groups introduced at the 5'-end of the probes using a one-step reaction method described by Chu et al. (Chu, B. C. F., and Orgel, L. E. (1985) DNA 4, 327–331.), results in a greater nucleophilicity of the terminal primary amino group of the alkyl linker as compared to the amino functionalities of the bases. It was therefore expected that the carboxyl groups on the beads would react preferentially with these primary amino groups.

100 ug 5'-$NH_2$ modified probe in 600 ul of 0.1M imidazole-buffer pH 7, 0.1M EDC were added per mg of R452 carboxyl beads. The reaction mixtures were incubated for 20 hours at room temperature with gentle shaking.

(b) $NH_2$ modified probes were made using Applied Biosystem synthesizer and AMINOLINK II.

The coupling reactions were as follows:

10 µg 5'$NH_2$ modified probe in 100 µl of 0.1M imidazole buffer pH 7.0, 0.1M EDC was added per mg of R452 carboxyl beads. The reaction mixtures were incubated for 20 hours at room temperature on a roller mixer (Coulter) followed by washing in TE buffer containing 0.1M NaCl (4×).

Hybridization efficiency:

A range of beads with different amount of probe attached were tested in hybridization experiments with a complementary 25 mer polydT probe.

The beads covered the range 1–250 pmol probe attached per mg beads.

Increasing amounts of 25 mer polydA oligonucleotide hybridized with increasing amounts of probe attached. 193 pmol hybridized to beads with 250 pmol attached. However, when the target molecule was in the range of 1000 bp (control mRNA Promega Corporation) there was no difference in hybridization efficiency between the bead with 100 pmol of attached probe compared with the more densely coupled beads.

EXAMPLE 2

Carbodiimide (EDC) mediated attachment of 5'-phosphate-probes to amino beads.

Probes were attached via a phosphoramidate linkage to 3 different amino beads by the method described by Ghosh et al. (Ghosh, S. S., and Musso, G. F. (1987) Nucl. Acids Res. 15, 5353–5372.). The amount of DNA attached to the different beads varied from 1.4–11.3 micrograms/mg.

The R469 beads which carry an amino group at the termini of an polyethylene glycol linker (8 atoms), bind a larger amount of probes than R240 beads which carry the amino group on a shorter linker (3 atoms), when the linker is made longer (number of atoms 20) as in the case of for the R442 beads, a decrease in the amount of probes bound to the beads is observed. This is probably due to secondary structures of the linkers which results in the terminal amino group becoming unavailable for coupling.

The amount of non-specifically bound DNA varies among the beads (7–30%) probably according to number of amino groups per unit of surface area. The R469 beads, which bind the largest amount of probes covalently (11 ug/mg), showed the lowest non-specific binding.

The acid lability of the phosphoramidate bond (Chu, B. C. F., Wahl, G. M., and Orgel, L. E. (1983) Nucl. Acids Res. 11, 6513–6529.) is used for measuring degree of end-attachment by acid hydrolysis. The amount of end-attached probes varies between the different beads from 20–65%, and again, the R469 bead seems to be the preferable one with 65% of the probes end-attached.

We were able to attach twice as much probe material to the R469 beads by performing the reaction in imidazole buffer pH 7 for 3 hours at 50° C., instead of pH 6, for 24 hours at room temperature. An increase in molarity of EDC from 0.1M to 0.2M resulted in a 20% decrease in amount of probes on the R469 beads (data not shown).

General Method 600 pmole (6 ug) of oligo A (36 mer) were dissolved in 1 ml of 0.1M imidazole, pH 7, 0.1M EDC and mixed with 5 mg of amino beads, and incubated for 3 hours at 50° C.

EXAMPLE 3

Coupling of 5'NH$_2$ probes to tosyl activated beads

NH$_2$ groups were introduced at the 5' end of oligonucleotides using Applied Biosystems DNA Synthesizer 381A and AMINOLINK II to introduce the primary NH$_2$ group at the 5' end. AMINOLINK II is supplied from Applied Biosystems. After synthesis these amino modified oligonucleotides were used directly in the coupling experiment.

Tosyl activated M-280 beads are commercially available from DYNAL AS, Oslo.

Coupling procedure:

10 mg of tosyl activated beads were mixed with 50 μg NH$_2$ modified oligonucleotide in 100 μl 0.5M Na$_2$HPO$_4$ and incubated at 37° C. for 20 hours on a roller mixer (Coulter) followed by washing in TE buffer containing 0.1M NaCl (4×).

EXAMPLE 4

Direct synthesis

DYNABEADS R 488 beads were used. They are the same beads as M-280 except that the diameter is 3.15 microns instead of 2.8 microns and they contain primary OH groups on the surface as in the M-280 beads.

Using the synthesizer (Pharmacia GENE ASSEMBLER) the 3' end of DNA will be attached to the surface.

Only small modifications were necessary to fit the 3.15 micron beads. In the standard small scale column from Applied Biosystems teflon filters with cut off at 3.0 microns were installed, the beads loaded and the column assembled.

Since this support does not contain dimethyltrityl (DMTr) groups and this machine stops if no such chemical is released in the first steps in the first cycle, small modifications in the start procedure were introduced. The synthesis was started using a standard ABI small scale column until the DMTr groups were released. Then the GENE ASSEMBLER was stopped manually and the modified column with magnetic beads was put into the GENE ASSEMBLER. The standard synthesis programme as recommended by the manufacturer was then followed. Deprotection was as recommended by Pharmacia. Direct synthesis was used to produce oligo(dT)$_{25}$ and the following sequence from the C region of the kappa light chain gene:

5'-TCACTGGATGGTGGGAAGATGGATACAGTTG-GTGCA-3'.

EXAMPLE 5

Materials and methods

Magnetic beads

DYNABEADS M-280 Streptavidin (Dynal A. S., Box 158, N-0212 Oslo) were used as solid phase. These are monodisperse superparamagnetic polymer particles with a diameter of 2.8 μm covalently coupled with Streptavidin. They have a surface area of 4.3 m$^2$/g.

Biotin binding capacity

100 μl 6×SSPE (Standard saline with phosphate and EDTA; Maniatis) containing 1 nmol $^{14}$C-Biotin (Amersham) was added to 0.5 mg beads (prewashed in 6×SSPE) and placed on a roller mixer (Coulter) at room temperature for 15 minutes.

After two separate washes in 6×SSPE the fraction of bound $^{14}$C-Biotin was measured by scintillation counting.

Deoxyoligonucleotides

Deoxyoligonucleotides were synthesized on an Applied Biosystems 381A DNA synthesizer.

Chemicals were purchased from Applied Biosystems. 5'amino modified deoxyoligonucleotides were made using AMINOLINK II.

The immunoglobulin light kappa chain probe used was:

5-TCACTGGATGGTGGGAAGATGGATACAGTTG-GTGCA-3'.

Biotinylation of Probes

Biotin XNHS ester (Clontec N-succinimidyl of N-biotinyl e-caproic acid) was used as recommended by the supplier.

0.1 μmol of NH$_2$-modified oligo(dT)$_{25}$ in 90 μl of water was added 10 μl labelling buffer (1M sodium bicarbonate/carbonate, pH 9.0) and vortexed.

Finally 25 μl Biotin XNHS ester (100 mg/ml) in dimethylformamide was added and incubated at room temperature overnight.

Excess labelling reagent and buffer was removed in a Sephadex G50 spin column.

The 5'Biotin oligo(dT)$_{25}$ was endlabelled using the fill in reaction by Klenow polymerase, α-[$^{32}$P]-dTTP and oligo (dA)$_{25}$ as template. Excess label was removed using a Sephadex G50 spin column.

Preparation of oligo(dT) Dynabeads (T-beads)

200 μg Biotinylated oligo(dT)$_{25}$ (24 n mol) in 2.5 ml 6×SSPE was mixed with 50 mg prewashed DYNABEADS M-280 Streptavidin and incubated on a roller mixer for 15 minutes at room temperature.

After two washes in 6×SSPE the beads were stored at 4° C. in 6×TE, 0.1% SDS.

Oligonucleotide hybridization assay

In the standard assay to measure hybridization capacity of different batches of T-beads, 0.1 mg of the beads in an eppendorf tube was washed once with 6×SSPE, 0.1% SDS. A magnet rack (MPC-E, Dynal A. S., Oslo) was used to aggregate beads between each step.

After removal of the washing buffer, 50 μl hybridization solution (6×SSPE, 0.1% SDS), containing 50 pmol of oligo (dA)$_{25}$ with trace amount (1–2×10$^5$ cpm) α-[$^{32}$P]-dATP-labelled oligo(dA)$_{25}$ was added.

After gentle mixing the tube was left to hybridize for two minutes at room temperature.

The hybridized beads were washed twice with 2×SSPE, 0.1% SDS at room temperature and the percentage of oligo(dA)$_{25}$ hybridized to the oligo(dT)$_{25}$ DYNABEADS was measured in a scintillation counter.

Labelling of poly A mRNA tracer 1 μg 1200 bp mRNA with a 3'polyA$_{30}$ tail (Promega) was mixed with 2.5 pmol oligo (dT)$_{25}$ in 10 μl 5×Klenow buffer, 1 u RNasin (Promega), 10mM DDT. After two minutes at room temperature 10 μCi α-[$^{32}$P]-dATP, 1 u Klenow polymerase (Amersham) and water up to 50 μl were added and incubation continued for 60 minutes at 15° C. Excess α-[$^{32}$P]-dATP was removed using a Sephadex spin column.

Buffers for poly(A) mRNA hybridization to Dynabeads M-280 Streptavidin coupled with oligo (dT)$_{25}$ Poly(A) binding buffer:
0.5M LiCl, 10 mM Tris-Cl, pH 7.5, 1 mM EDTA, 0.1% sodium dodecylsulphate.

Middle wash buffer:
0.15M LiCl, 10 mM Tris-Cl, pH 7.5, 1 mM EDTA, 0.1% sodium dodecylsulphate.

Elution buffer: 2 mM EDTA, 0.1% SDS. Depending on the subsequent use of the purified mRNA SDS may be omitted in the last washing step and in the elution buffer.

EXAMPLES 6-8

The following RNAs are utilized to separately prepare complementary DNA: (I) Reference mRNA supplied with RIBOCLONE™ cDNA SYNTHESIS SYSTEM (Promega, Madison Wis., USA), (II) mouse pancreas mRNA (Clonetec, USA), or (III) hybridoma AB1 crude RNA extract, prepared from 2×10$^7$ AB1 cells by the method of Maniatis et al. supra, pages 187-196. 1 μg of samples I and II, and 10 μg of sample III, each in 100 μl 6×SSPE are warmed at 100° C. for 3 minutes, then quenched in ice-water. Each solution is separately added to 1 mg of magnetic beads R502 carrying the following probe attached via a 5'-amino group to carboxyl groups on the beads by EDC coupling:

5'-NH$_2$—(CH$_2$)$_{12}$—GACCTTGGGAATTCCCCGGGCTGCAGT(T)$_{24}$)-3.

ECORI    SmaI    PstI

Hybridisation of the beads probe to the RNA in the samples is allowed to proceed at room temperature for 10 minutes. The probe is then retrieved with a magnet, and washed twice with 2×SSC at room temperature. First and second strand cDNA synthesis are performed according to the RIBOCLONE™ cDNA Synthesis System Technical Manual, described as follows. For a total volume of 25 μl, the following components are combined with the magnetic probe-linked template RNA in a sterile RNase-free microcentrifuge tube on ice in the following order to form a first strand synthesis mixture:

| Component | Amount |
| --- | --- |
| Nuclease-free water to a final volume of | 25 ul |
| 10x first strand buffer (500 mM Tris-HCl, pH 8.3 (42° C.), 750 mM KCl, 100 mM MgCl$_2$, 5 mM spermidine) | 2.5 ul |
| 100 mM dithiothreitol | 2.5 ul |
| 40 mM Na pyrophosphate | 2.5 ul |
| 10 mM dNTP mixture | 2.5 ul |
| RNasin ribonuclease inhibitor | 25 units |
| Reverse transcriptase | 15 units/ug RNA |

The above components are mixed gently with the magnetic probe-linked template RNA. 5 ul of the mixture is optionally removed to another tube containing 2–5 ul Ci of (α-$^{32}$P) dCTP (400 Ci/mmol) which has either been dried down or is in less than 1 ul volume. This aliquot of the first strand synthesis mixture is used as a tracer reaction, that is, it may be used to measure first strand synthesis by (α-$^{32}$P) dCTP incorporation, utilising trichloroacetic acid precipitation and alkaline agarose gel electrophoresis as more fully described in the aforementioned RIBOCLONE™ Technical Manual. Both the main reaction and tracer reaction tubes are incubated at 40° C. for 60 minutes and then are placed on ice. 1ul of 0.2M EDTA is then added to the tracer reaction. The tracer reaction is diluted to a total volume of 20 ul with water and stored on ice. At least 3 ul of the tracer reaction mixture may be used for the incorporation assay described more particularly in the aforesaid RiboClone™ Technical Manual. The remaining 17 ul may be used for gel analysis after extraction as described in the RIBOCLONE™ Technical Manual.

To the first strand main synthesis mixture tubes containing magnetic probe-linked RNA/DNA hybrids the following components are added in the following order to carry out second strand synthesis:

| Component | Amount |
| --- | --- |
| (first strand synthesis mixture) | (20 ul) |
| nuclease-free water to a final volume of 10x second strand buffer (400 mM Tris-HCl, pH 7.2 850 mM KCl, 30 mM MgCl$_2$, 1 mg/ml bovine serum albumin, 100 mM (NH$_4$)$_2$SO$_4$) | 100 ul |
| 100 mM dithiothreitol | 3 ul |
| 1 mM nicotinamide adenine dinucleotide | 10 ul |
| E. coli RNase H | 0.8 units |
| E. coli DNA polymerase I | 23 units |
| E. coli ligase | 1 unit |
| *(α-$^{32}$P)dCTP (400 Ci/mmol) | 205 uCi |

*The radioactive nucleotide is optionally used in a separate aliquot of the above mixture for measurement of second strand synthesis.

The above components are mixed gently and incubated at 14° C. for 2 hours. The mixture is then heated to 70° C. for 10 minutes, and the contents at the bottom of the tube are collected by brief centrifugation and placed on ice. In order to create a blunt end on the ds cDNA terminus distal from the magnetic particle, 2 units of T4 polymerase per ug of input RNA is added to the mixture, which is incubated at 37° C. for 10 minutes. The blunt-ending reaction is stopped by adding 10 ul 0.2M EDTA. The mixture is placed on ice. At this point, 5 ul of the mixture may be derived for incorporation assay as described in the RiboClone™ Technical Manual. The magnetic probe/ds cDNA complex is retrieved with a magnet and washed with ligase buffer.

A restriction enzyme adaptor incorporating a HindIII RE site is then ligated to the distal end of the magnetic probe/ds cDNA complex using T4 DNA ligase at 37° C. in ligase buffer. The HindIII and PstI RE sites are then cleaved using the appropriate enzymes to simultaneously cleave the cDNA from the magnetic particles and provide the required sticky end at the distal terminus. The magnetic particles are then removed by magnetic attraction.

The cDNA synthesis method of the invention may be used as follows for the preparation of cDNA from specific genes having known or partially known DNA sequence.

EXAMPLE 9

The mRNA for the kappa-light chain of monoclonal antibody AB1, which antibody is specific for a B-cell differential antigen, is isolated for cDNA synthesis as follows:

Total crude RNA is extracted from AB1 cells by the LiCl-urea method described by Auffray et al., Eur. J. Biochem. 107, pages 303-314 (1980). 10 ug of the resulting total RNA preparation in 100 ml 6×SSPE is heated at 95° C. for 5 minutes, quenched on ice, and added to 1 mg of a magnetic probe containing the nucleotide sequence for the C-region of the kappa light chain gene: 5'-NH$_2$-TCACTGGATGGTGGGAAGATGGATACAGTTGGTGCA-3'. The probe sequence is prepared with a 5'-terminal amino group using an Applied Biosystem DNA synthesis machine, using, for example, 12-MM Tritylaminododecyl-cyanoethyl NN-diisopropyl phosphoramidate to introduce a group-OPO$_2$(CH$_2$)$_{12}$NH$_2$ the 5'-OH group grouping. The probe sequence is coupled to a magnetic bead through the 5'-NH$_2$ terminus as in Example 2. The magnetic probe/template RNA reaction mixture is allowed to hybridise for 10 minutes at room temperature. Hybrids are collected and washed twice in 500 ul 2×SSC at room temperature. Following washing, 160 ul 6×SSPE is added to the mixture and the magnetic probe is melted away from the target kappa-light chain mRNA by heat treatment at 95° C. for 5 minutes. The probe is then collected by magnetic attraction. The supernatant containing the kappa-light chain mRNA is added to an oligo(dT)$_{25}$ magnetic probe as described in Examples 2–4 containing three RE sites between the magnetic particle and the oligo(dT)$_{25}$ sequence. The mixture is allowed to hybridize for 10 minutes and the procedure of Example 1 is followed to prepare ds cDNA fragments. These fragments are subsequently ligated into the cloning vector pGEM-3Z and used to transform E. coli.

EXAMPLE 10

0.5 mg of a 5% suspension of PANDEX AVIDIN PARTICLES (0.77 μm in diameter, (Baxter Healthcare Corp, Mundelein, Ill., USA)) in phosphate buffered saline (PBS) were mixed with 500 pmol of 5'biotinylated oligo-dT$_{25}$ and incubated at room temperature for 15 minutes. All sedimentation and washing procedures were performed using an Eppendorf centrifuge for 3 minutes. The particles were washed twice in 100 μg PBS to remove excess free oligonucleotide.

100 μg of the pandex oligo-dT particles and 0.5 μg Promega control mRNA (a 1.2 kb kanamycin RNA containing 30 A residues as polyA 3'tail) were treated as described in Example 2 but with the only difference that instead of a magnetic separation step with magnetic beads, a 3 minutes eppendorf centrifugation step was introduced in order to wash and change buffers. Incubation of aliquots of first and second strand buffer with ($\alpha^{32}$P) dCTP made it possible to follow the cDNA synthesis.

The gene coding for the above rRNA contains a HindIII restriction site. After cDNA synthesis on the pandex particles when the first strand was labelled using ($\alpha^{32}$p)dCTP, incubation was effected with HindIII to test the quality of the newly synthesised cDNA. The pandex beads with cDNA attached, were incorporated in the ($\alpha^{32}$p)dCTP first strand, treated with HindIII and the supernatant run on a 1.5% agarose gel. A distinct band of expected size was visualized on an X-ray film.

EXAMPLE 11

The purpose of this experiment is to make a subtraction cDNA library corresponding to genes that are transcribed in the differentiated B-cell line "Raji" but not in the stem cell line KM3.

Construction of "magnetic" 1.strand cDNA library from the KM-3 cell line

PolyA mRNA from the KM-3 cell line and the Raji cell line was purified using magnetic beads. 7 μg of the purified KM-3 mRNA, 5 ng unique control mRNA (Promega RIBOCLONE kit), was added to 5 mg of magnetic beads, R502, carrying an oligo dT$_{36}$-nucleotide probe, with a resulting hybridization capacity of 16 pmols per. mg beads.

The hybridization was carried out in 200 μl 6×SSPE for 10 minutes at room temperature. The beads were washed once in 500 μl 6×SSPE at 40° C. for 5 minutes to remove nonspecific binding and unbound mRNA.

The beads were then resuspended in 100 μl 1.strand cCNA synthesis buffer and components as supplied by the Promega Riboclone kit as follows:

| Component | Amount |
| --- | --- |
| Nuclease-free water to a final volume of | 100 μl |
| 10x first strand buffer (500 mM Tris-HCl, pH 8.3 (42° C.), 750 mM KCl, 100 mM MgCl$_2$, 5 mM spermidine) | 10 μl |
| 100 mM dithiothreitol | 10 μl |
| 40 mM Na pyrophosphate | 10 μl |
| 10 mM dNTP mixture | 10 μl |
| RNasin ribonuclease inhibitor | 50 units |
| Reverse transcriptase | 75 units |
| 10 μCi α-[$^{32}$P]-dATP (Amersham) | |

The above components were gently mixed with the magnetic probe-hybridized template RNA and incubated at 42° C. for 60 minutes. The beads were now collected by magnet and washed once in 500 μl TE (10 mM Tris-HCl pH 7.4, 1 mM EDTA) to remove excessive reagents and twice in 500 μl 0.2N NaOH, 0.5N NaCl to remove the template mRNA and finally resuspended in 200 μl 6×SSPE. Bead- bound radioactivity was measured to estimate the amount and effectiveness of the 1.strand cDNA synthesis. The magnetic 1.strand KM3 cDNA(ss) library was mixed with 200 pmols of an oligo dA$_{25}$-nucleotide and left to hybridize for 10 minutes at room temperature to cover the polydA region, 25–200 bases long, originating from the RET-primer and reverse transcribed polyA tail of the mRNA. This region is covered to avoid binding of the polyA tails of the Raji mRNA. After hybridization, excess oligo dA$_{17}$ is washed away in 6×SSPE at room temperature. After washing the beads were resuspended in 200 μl hybridization solution of the following composition:

50% formamide 5×Denhardt's solution (50×Denhardt's solution contains 5 g Ficoll, 5 g polyvinylpyrrolidone, 5 g Bovine Serum Albumin, water to 500 ml)

5×SSPE 0.1% SDS

2 μg purified polyA mRNA from the Raji cells and 1 ng radioactive labelled (50.000 cpm) control mRNA was added to the 1.strand library and left to hybridize at 42° C.

After 20 minutes incubation the solution was transferred to a 50° C. waterbath for 5 minutes to increase stignency. Then the beads with hybridized mRNA were collected by magnet. The "supernatant" was transferred to a new tube.

The remaining test mRNA in the supernatant was found to be 9% of the amount added, indicating that 90% of common homologous mRNA had been removed. This was even more than expected since we in this experiment started with a maximum of 3-fold excess of KM3 1.strand cDNA (from 6–7 μg mRNA) compared to 2 μg of Raji mRNA.

The beads carrying the KM3 1.strand cDNA library were regenerated by washing twice in 0.2N NaOH, 0.5N NaCl, resuspended in 6×SSPE, rehybridized with oligo (dA)$_{25}$, then added to the supernatant still containing 9% of common mRNA together with "subtraction" mRNA.

The second round of subtraction was carried out as the 1. round.

The resulting supernatant now contained less than 1% labelled tracer mRNA. (The exact percentage was uncertain due to low cpm-count). This extremely good result was expected since the KM3 1.strand cDNA's on the beads (still from 6-7 μg mRNA) now reacted with only 9% or 2 μg homologous mRNA giving a 30 fold molar excess. Since no further rounds of subtraction seemed to be necessary the supernatant with subtracted mRNA was added to 2 mg of fresh beads with RET oligonucleotide probe and hybridized at room temperature for 10 minutes.

After washing in 2×SSC at room temperature cDNA synthesis was performed.

A Hind III linker was ligated to the free end of the double-stranded cDNA, cleaved with Hind III enzyme and released from the beads with PstI cleavage. After separation from the beads the cDNA was now phenol extracted (to destroy restriction enzymes), ethanol precipitated and ligated into the shuttle cloning vector pCDM8.

After ligation the recombinant plasmids were transformed into E. coli. The transformed E. coli cells harboring the cloned subtraction cDNA library were (after 1 hour to allow antibiotic resistance phenotype expression) subjected to antibiotic pressure and amplified for 5 doubling times. Thereafter glycerol was added to 15%, the mixture divided into 0.5 ml batches, quickly frozen in liquid nitrogen and stored in −70° C. until further use.

We claim:

1. A process for the production of cDNA, comprising the steps of:
   (a) contacting a liquid containing mRNA with an insoluble support having DNA probes attached thereto via their 5' termini whereby mRNA in said sample is hybridized to said probes and thereby bound to said support, wherein:
      (A) said insoluble support comprises a plurality of particles that are comprised of: (i) superparamagnetic iron oxide dispersed within a polymer particle, (ii) nucleic acid-binding functional groups at the surface of said particle for bonding said probes and (iii) a coating to reduce non-specific binding;
      (B) said probes are bound to said particles via said functional group;
      (C) the particles in said plurality are monodisperse and the standard deviation of the diameter is less than 5%;
   (b) removing said liquid; and
   (c) adding enzymes and nucleotides in solution whereby said probe functions as a primer to produce single stranded cDNA on the mRNA templates.

2. A process as claimed in claim 1 in which the DNA probes comprise at their 5' ends a DNA sequence containing at least one restriction site.

3. A process as claimed in claim 1 wherein the probe is oligo-dT.

4. A process as claimed in claim 1 wherein the probe binds in a sequence specific manner to a target mRNA sequence.

5. A process as claimed in claim 4, in which the probe comprises a specific DNA sequence which is complementary to a sequence which occurs in a multiplicity of different mRNAs.

6. A process as claimed in claim 1 wherein the single stranded cDNA is subsequently converted into double stranded DNA.

7. A process as claimed in claim 1 for producing a cDNA subtraction library from two populations of cells which express mRNAs which differ in sequence, comprising the steps of:

a) contacting a liquid containing the total mRNA from a first one of said cell populations with said insoluble support carrying 5'-attached oligo-dT probes whereby said mRNA is hybridized thereto;

b) removing said liquid;

c) using said oligo-dT probes as a primer and adding enzymes and nucleotides in solution whereby corresponding single strands of cDNA are formed and removing the hybridized mRNA to provide a first strand cDNA library attached to said insoluble support;

d) contacting the insoluble support carrying said attached first strand cDNA with a liquid containing the total mRNA of the second one of said two cell populations to hybridize mRNA present in both cell populations and e) removing the insoluble support and attached mRNA to leave in solution those mRNA molecules present only in said second cell population that do not hybridize to said cDNA;

f) making said cDNA subtraction library from said mRNA remaining in solution.

8. A process as claimed in claim 7 wherein the insoluble support bearing the cDNA library at step c) is treated with oligo-dA before step d) to avoid non-specific mRNA binding.

9. A process as claimed in claim 1 which includes washing steps and changes of buffer to optimise hybridisation and enzyme activity.

10. A kit for cDNA synthesis comprising:
   (a) an insoluble support having DNA probes attached thereto, and one or more of the following:
   (b) a reverse transcriptase;
   (c) a polymerase and optionally a ligase and/or a nuclease;
   (d) deoxynucleotides, and
   (e) buffers suitable for reverse transcription and/or polymerization
   wherein said insoluble support comprises a plurality of particles that are comprised of: (i) superparamagnetic iron oxide dispersed within a polymer particle, (ii) a nucleic acid-binding functional group at the surface of said particle for bonding said probes and (iii) a coating to reduce non-specific binding; said probes are bound to said particles via said functional group, and the particles in said plurality are monodisperse and the standard deviation of their diameter is less than 5%.

11. A process for the production of cDNA, comprising the steps of:
   (a) contacting a liquid containing mRNA with monodisperse, superparamagnetic particles carrying a single stranded 5'-attached DNA probe capable of binding to said mRNA;
   (b) removing said liquid;
   (c) contacting said particles with an aqueous solution of a reverse transcriptase or polymerase in the presence of labelled nucleotides using the probe as a primer whereby labelled complementary single stranded DNA is formed if said mRNA was present in said liquid, wherein a predetermined amount of dideoxyunucleotides are present to limit chain synthesis to a predetermined average length thereby enabling the total amount of label to be correlated with the number of target nucleic acid molecules;
   (d) magnetically aggregating said particles onto a surface and removing said solution; and (e) determining the amount of said label in said complementary single stranded DNA.

12. A process as claimed in claim 11 for producing a cDNA subtraction library from two populations of cells which differ in their mRNAs, comprising the steps of:

(a) contacting a liquid containing total mRNA from a first one of said cell populations with said monodisperse superparamagnetic particles carrying 5'-attached oligo-dT probes whereby substantially all said mA is hybridized thereto;

(b) removing said liquid;

(c) using said oligo-dT probes as a primer and adding enzymes and nucleotides in solution whereby corresponding single strands of cDNA are formed and removing the hybridized mRNA to provide a first strand cDNA library attached to said monodisperse superparamagnetic particles;

(d) contacting the monodisperse superparamagnetic particles carrying said attached first strand cDNA with a liquid containing total mRNA of a second one of said two cell populations to hybridize mRNA to the first strand cDNA; and (e) removing the monodisperse superparamagnetic particles and attached mRNA to leave in solution those mRNA molecules present only in said second cell population that do not hybridize to said cDNA;

(f) making said cDNA subtraction library from said mRNA remaining in solution.

* * * * *

UNITED STATES PATENT AND TRADEMARK OFFICE
CERTIFICATE OF CORRECTION

PATENT NO. : 5,759,820
DATED : June 2, 1998
INVENTOR(S) : Erik HORNES, et al.

It is certified that error appears in the above-identified patent and that said Letters Patent is hereby corrected as shown below:

Please note on front cover, Item [ * ] Notice: delete "The term of this patent shall not extend beyond the expiration date of Pat. No. 5,572,439" and replace with -- The term of this patent shall not extend beyond the expiration date of Pat. No. 5,512,439--.

Signed and Sealed this

Twelfth Day of December, 2000

Attest:

Q. TODD DICKINSON

*Attesting Officer*  *Director of Patents and Trademarks*